United States Patent
Koh et al.

(10) Patent No.: US 7,200,442 B1
(45) Date of Patent: Apr. 3, 2007

(54) IMPLANTABLE CARDIAC DEVICE WITH IMPEDANCE MONITORING CONTROL AND METHOD

(75) Inventors: Steve Koh, South Pasadena, CA (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 287 days.

(21) Appl. No.: 10/938,012

(22) Filed: Sep. 10, 2004

(51) Int. Cl.
*A61N 1/08* (2006.01)

(52) U.S. Cl. .................................... 607/28
(58) Field of Classification Search ............. 600/481, 600/506, 508, 509; 607/6, 8, 28
See application file for complete search history.

(56) References Cited

U.S. PATENT DOCUMENTS

| | | | | |
|---|---|---|---|---|
| 5,713,935 A | * | 2/1998 | Prutchi et al. | 607/28 |
| 5,910,156 A | * | 6/1999 | Cinbis et al. | 607/27 |
| 6,445,951 B1 | * | 9/2002 | Mouchawar | 607/28 |
| 6,574,507 B1 | | 6/2003 | Bonnet | 607/20 |
| 2002/0193697 A1 | * | 12/2002 | Cho et al. | 600/529 |
| 2003/0130589 A1 | | 7/2003 | Poezevera | 600/533 |

FOREIGN PATENT DOCUMENTS

WO   WO 02/087433 A1   11/2002

* cited by examiner

*Primary Examiner*—Robert E. Pezzuto
*Assistant Examiner*—Eric D. Bertram

(57) ABSTRACT

An implantable cardiac device having an impedance monitor has an impedance monitoring control. The impedance monitor includes a pulse generator that applies a current between a pair of implanted electrodes and an impedance measuring circuit that measures impedance across the implanted electrodes and provides an impedance signal during a present time that the pulse generator applies the current between the pair of implanted electrodes. The impedance monitoring control processes the impedance signal to provide impedance monitoring characteristic results and compares the results to preset standards. A control circuit varies the operating parameters of the impedance monitor responsive to the comparison of the impedance monitoring characteristic results to the present standards.

3 Claims, 5 Drawing Sheets

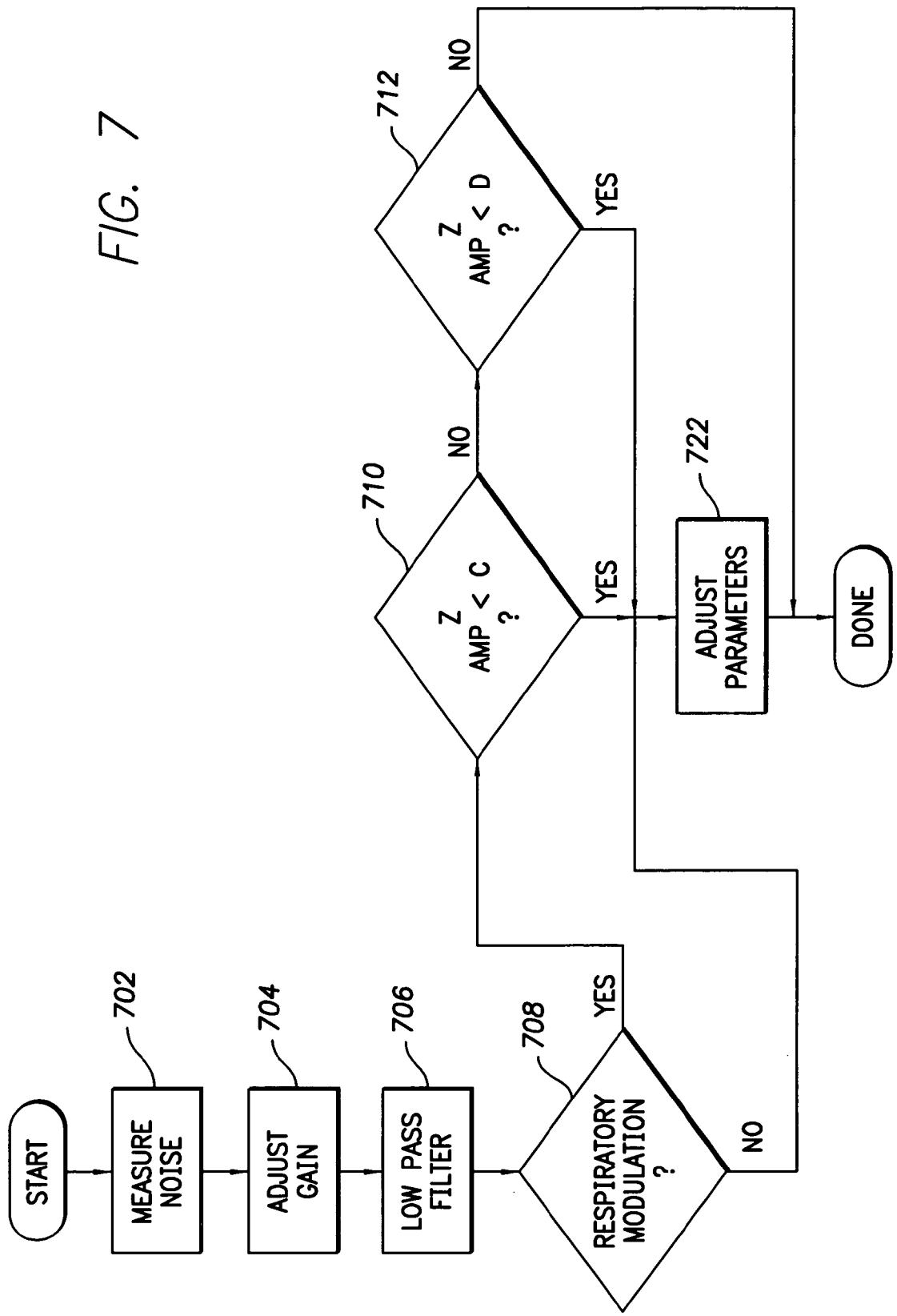

IMPLANTABLE CARDIAC DEVICE WITH IMPEDANCE MONITORING CONTROL AND METHOD

FIELD OF THE INVENTION

The present invention generally relates to implantable cardiac devices having impedance monitoring. The present invention more particularly relates to impedance monitoring control for such devices to assure proper assessment of patient condition based upon impedance measurements.

BACKGROUND OF THE INVENTION

Implantable cardiac devices are well known in the art. They may take the form of an implantable defibrillator (ICD) to treat accelerated rhythms of the heart such as fibrillation, or an implantable pacemaker to maintain the heart rate above a prescribed limit, such as, for example, to treat a bradycardia. Implantable cardiac devices are also known which incorporate both a pacemaker and a defibrillator.

The devices are generally implanted in an upper portion of the left-side of the chest beneath the skin of a patient within what is known as a subcutaneous pocket. The implantable devices generally function in association with one or more electrode-carrying leads which are implanted within the heart. The electrodes are positioned within the heart, for making electrical contact with their designated heart chamber. Conductors within the leads couple the electrodes to the device to enable the device to deliver the desired therapy.

Implantable pacemakers may operate in unipolar or bipolar pacing polarity electrode configurations. In unipolar pacing, the pacing stimulation pulses are applied between a single electrode carried by the lead, in electrical contact with the desired heart chamber, and the pulse generator case. The electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

For defibrillation, one lead may include at least one defibrillation electrode arranged to be positioned in the right ventricle. When fibrillation is detected, a pulse generator delivers a defibrillating shock from the defibrillation electrode in the right ventricle to the device conductive housing to terminate the arrhythmia. Alternatively, a further defibrillation electrode ma be positioned in the right atrium or superior vena cava and electrically connected to the right ventricular defibrillation electrode. In this arrangement, the defibrillating shock is delivered from the parallel connected defibrillation electrodes to the conductive housing.

Congestive heart failure (CHF) is a debilitating, end-stage disease in which abnormal function of the heart leads to inadequate bloodflow to fulfill the needs of the body's tissues. As CHF progresses, blood pressure increases and interstitial fluid accumulates in the lungs around the heart. The accumulated fluid fills the gas air exchange space in the lungs and prevents proper lung function. Reduced oxygen saturation further aggravates cardiac function with possible infarction. Hence, CHF requires constant monitoring.

Sleep apnea is another condition which may benefit from constant or frequent monitoring. Sleep apnea is a serious, potentially life-threatening condition characterized by brief interruptions of breathing during sleep. In a given night, the number of involuntary pauses in breathing (apneic events) may be as high as twenty to sixty or more per hour. During sleep apnea, poor oxygen saturation sends a "wake-up call" to the brain to reinitiate breathing. However, as oxygen saturation restores to a normal level inducing deeper sleep, the stage is again set for repeated sleep apnea.

As is known, CHF disease state may be evaluated through impedance measurements utilizing electrodes implanted in the heart. Such measurements may be carried out by applying a current between a pair of the electrodes and measuring the voltage therebetween. An implanted cardiac stimulation device is well suited for such an application. Sleep apnea may also be monitored in this manner.

The current applied between the electrodes must have an amplitude sufficient to induce a detectable and usable voltage across the electrodes. However, the current application and voltage measurement must be performed in such a manner that impedance monitor voltages also remain in the active, non-saturated ranges of the monitoring components. Saturation or rail to rail voltages can make impedance measurements unsuitable for proper CHF or apnea assessment.

SUMMARY

An implantable cardiac device is described having an impedance monitoring control. The device comprises an impedance monitor comprising a pulse generator that applies a current between implanted electrodes and an impedance measuring circuit that measures impedance across implanted electrodes and provides an impedance signal during a preset time that the pulse generator applies the current between the implanted electrodes, a processor that processes the impedance signal to provide impedance monitoring characteristic results, a comparator that compares the impedance monitoring characteristic results to preset standards, and a control circuit that varies operating parameters of the impedance monitor responsive to the comparison of the impedance monitoring characteristic results to the present standards. In one embodiment, the current is applied between the same pair of electrodes that are used to measure the impedance (voltage) resulting from the applied current.

In another embodiment, an implantable cardiac device comprises an impedance monitoring control. The impedance monitoring control comprises an impedance monitor comprising a pulse generator that applies a current between a pair of implanted electrodes and an impedance measuring circuit that measures impedance across the implanted electrodes and provides an impedance signal during a preset time that the pulse generator applies the current between the pair of implanted electrodes. The device further comprises a processor that processes the impedance signal to provide impedance monitoring characteristic results, a comparator that compares the impedance monitoring characteristic results to preset standards, and a control circuit, responsive to the comparison of the impedance monitoring characteristic results to the preset standards, that determines if the impedance signal represents a normal condition permitting operating parameters of the impedance monitor to remain unchanged, or an abnormal signal condition, requiring adjustment of the impedance monitor operating parameters.

The normal condition may be one of a normal breathing condition and a sleep apnea condition. The abnormal signal condition may be one of a rail to rail signal condition, a saturated signal condition, and a noisy signal condition.

The device may further comprise a therapy circuit that provides sleep apnea therapy responsive to a determination of a sleep apnea condition. The sleep apnea therapy may be vagus or phrenic nerve stimulation.

The impedance monitor may further include an input amplifier having a gain and a DC offset voltage. The operating parameters may include input amplifier gain and DC offset voltage. The operating parameters may alternatively or in addition include applied current amplitude and applied current pulse width.

In yet another embodiment, a method comprises applying a current between a pair of implanted electrodes, sensing a voltage across the implanted electrodes to provide an impedance signal during a preset time that the current is applied between the pair of implanted electrodes, and processing the impedance signal to provide impedance monitoring characteristic results. The method further comprises comparing the impedance monitoring characteristic results to preset standards, and varying the application of the current between and/or the sensing of the voltage across the pair of implanted electrodes responsive to the comparison of the impedance monitoring characteristic results to the present standards.

BRIEF DESCRIPTION OF THE DRAWINGS

Further features and advantages of the present invention may be more readily understood by reference to the following description taken in conjunction with the accompanying drawings, in which:

FIG. 7 is a flow diagram of a noise treatment subroutine of FIG. 6.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
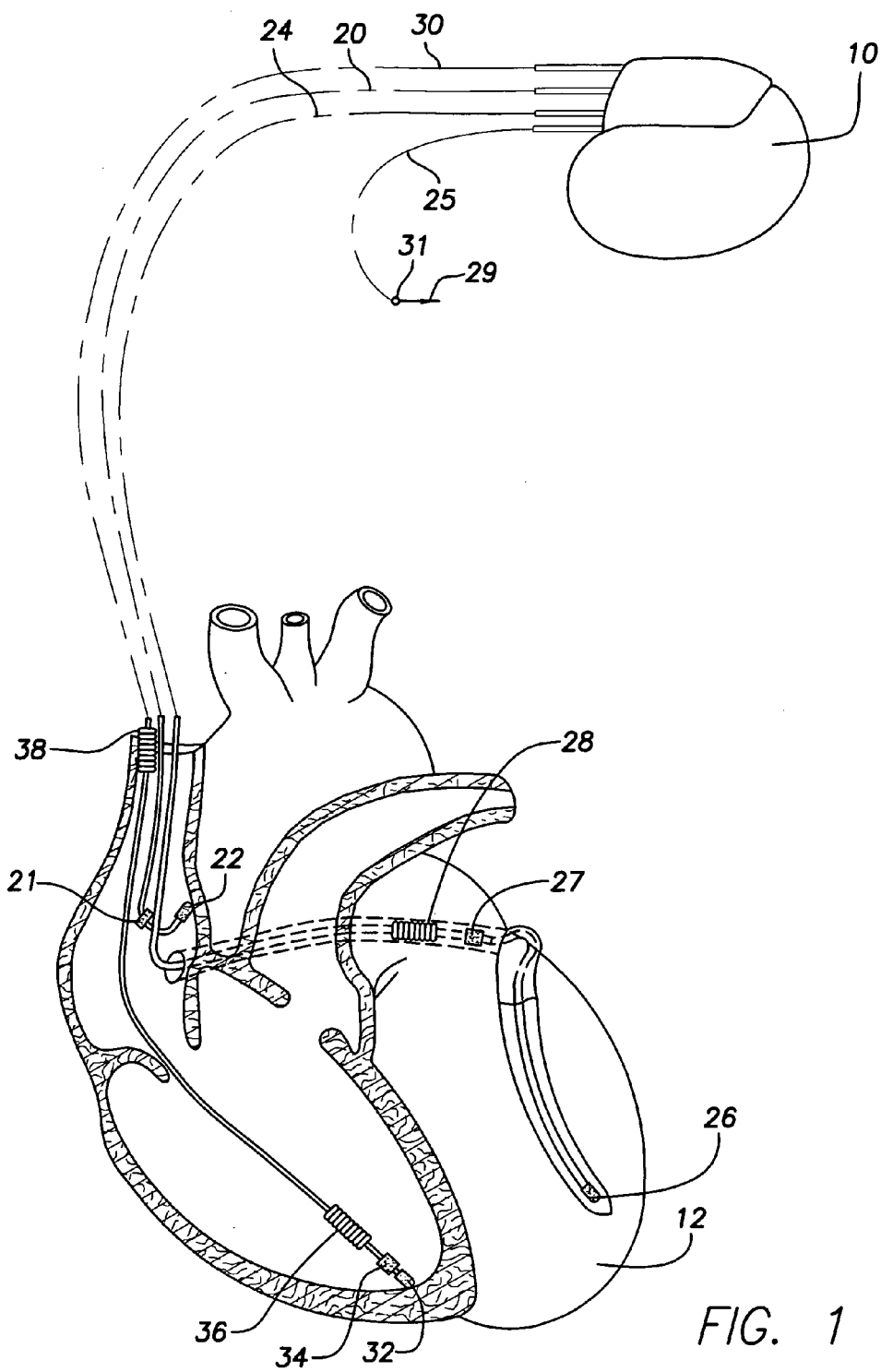
FIG. 1 is a simplified diagram illustrating an implantable stimulation device embodying the present invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial ring electrode 21 and an atrial tip electrode 22, which are typically implanted in the patient's right atrial appendage. The electrodes 21 and 22 form a bipolar electrode pair useful for right atrial pacing and near field targeted atrial activity sensing.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

The device 10 includes a still further lead 25. The lead 25 includes a distal electrode 29 and a proximal electrode 31. The electrodes 31 and 29 may be coupled to the nervous system of the patient for applying vagal/phrenic nerve stimulation therapy when required and as described hereinafter.

Figure 2:
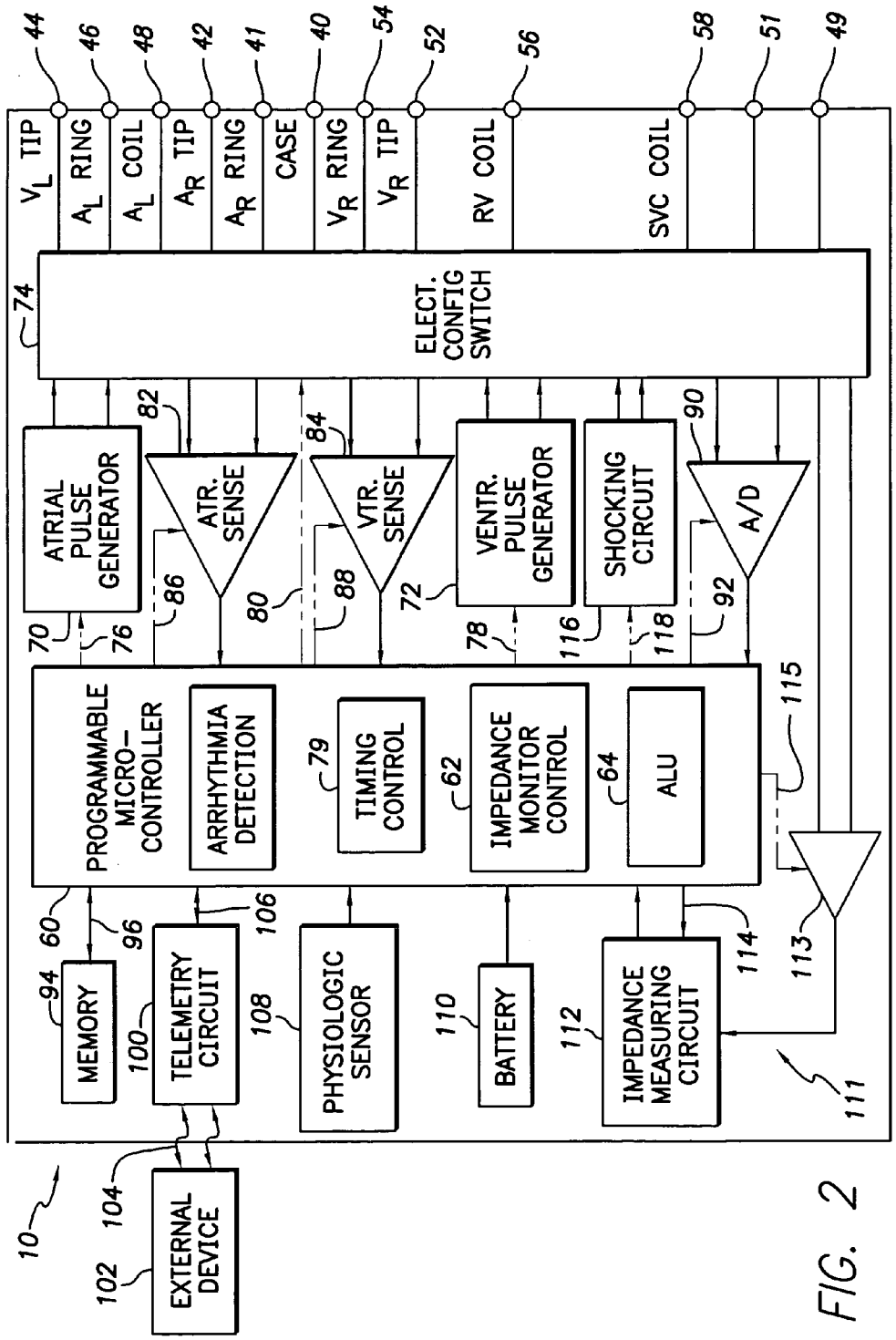
FIG. 2 is a functional block diagram of the implantable stimulation device of FIG. 1 according to one embodiment of the invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 47, 48, 49, 52, 54, 56, and 58 (shown schematically and, for convenience, the names of the electrodes to which they are connected are shown next to the terminals). As such, to achieve right atrial sensing and pacing, the connector includes at least a right atrial ring terminal ($A_R$ RING) 41 and a right atrial tip terminal ($A_R$ TIP) 42 adapted for connection to the atrial ring and tip electrodes 21 and 22, respectively.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. Lastly, to achieve vagal or phrenic nerve stimulation, the electrode 31 may be coupled to terminal 51 and the electrode 29 may be coupled to terminal 49.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

As further shown in FIG. 2, and according to this embodiment, the device 10 includes an impedance monitor 111 including an impedance measuring circuit 112 and an input amplifier 113. The monitor 111 is enabled by the microcontroller 60 via a control signal 114. As is known, the impedance monitor 111 may be used for lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. For example, according to this embodiment, the case 40 may serve as one impedance monitoring electrode, and one of electrodes 32, 34, or 36 may be employed as the second impedance monitoring electrode.

More specifically, to measure impedance for ascertaining CHF progression or regression status or sleep apnea, the impedance monitor 111 apply a current between at least two electrodes, as for example among those previously mentioned, and selected by switch 74. As the current is applied, the induced voltage across the electrodes is sensed by the input amplifier 113. The impedance may then be determined in a known manner. An ideal impedance may be, for example, about fifteen ohms, but may vary with specific patients and measuring techniques.

To make sure that accurate impedance measurements are being made and to assure accurate patient condition assessment, the device further includes an impedance monitor control 62 according to this embodiment.

As will be seen subsequently, the impedance monitor control 62 causes the impedance monitor 111 to apply a known constant current between the electrodes used for impedance monitoring. The input amplifier 113 continuously monitors the voltage across these electrodes to enable the impedance measuring circuit 112 to generate an impedance signal during the duration of the applied current. An arithmetic logic unit 64 (ALU) processes the impedance signal to generate impedance monitoring characteristic results. The ALU 64 then compares these results to preset standards. The monitor control 62 then, responsive to the comparisons, varies or adjusts operating parameters of the impedance monitor 111 to assure its proper operation. The operating parameters subject to adjustment may include, for example, applied current amplitude, applied current frequency, applied current pulse width, the gain of input amplifier 113 and the DC offset of the input amplifier 113. The adjustment of the current amplitude, frequency, and pulse width may be made over line 114 and the adjustment of the input amplifier 99 gain and DC offset may be made over line 115. The applied current may be provided from one of the pulse generators 70 and 72 or from the shocking circuit 116.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
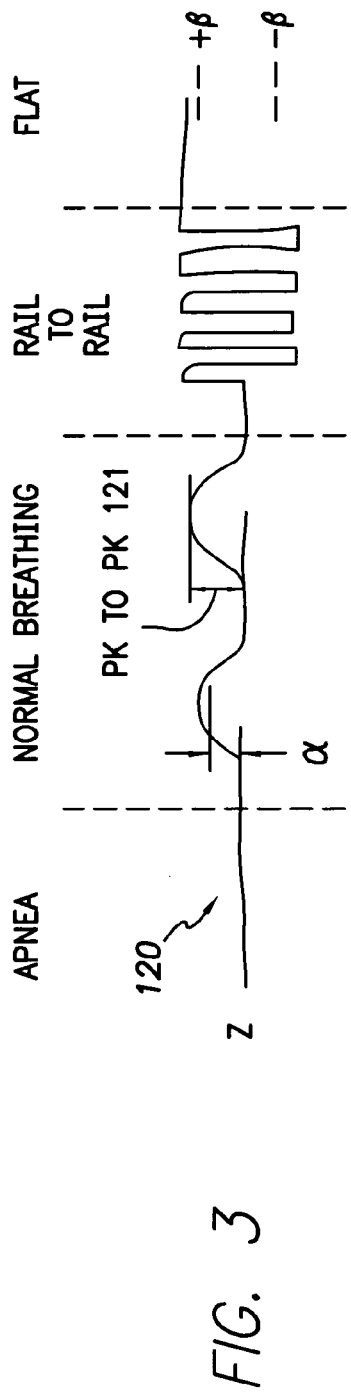
FIG. 3 is an illustrative impedance signal during apnea, normal breathing, a rail to rail condition and a saturation condition.

FIG. 3 shows an illustrative impedance signal during apnea, normal breathing, a rail to rail condition and a flat or saturated condition. During apnea, the impedance is at a low and substantially constant level due to the lack of breathing and hence physiologic movement of the patient's chest cavity. During normal breathing, there is a rhythmic undulation in the impedance signal in keeping with the cyclical movement of the patient's chest. Here it may be seen that the ALU compares the impedance signal to a minimum impedance amplitude threshold ($\alpha$) and the monitor control measures a peak to peak impedance signal amplitude 121. The ALU further compares the impedance signal to a maximum impedance amplitude threshold, $+\beta$ and $-\beta$.

Figure 4:
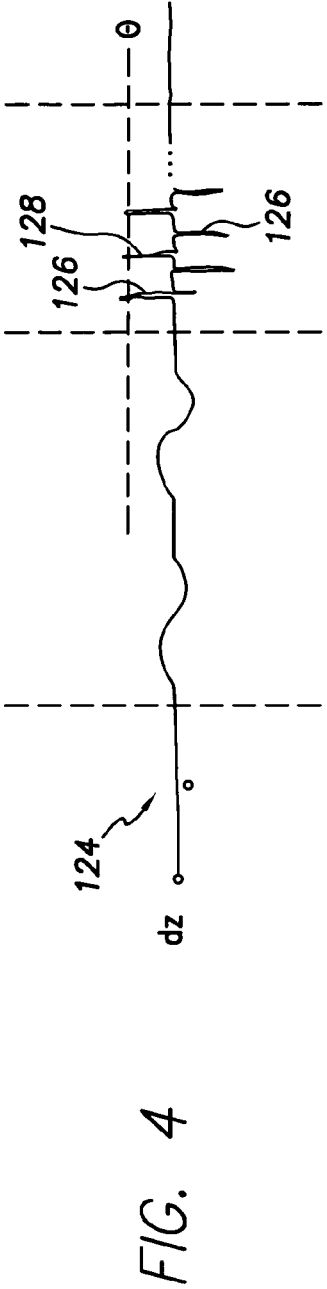
FIG. 4 is a differentiation signal representing the differentiation of the impedance signal of FIG. 3.

FIG. 4 shows a signal corresponding to the differentiation of the impedance signal 120 (Z) to provide a differential signal (dZ) 124. During apnea, the amplitude of signal 124 is essentially zero. During normal breathing, the signal 124 smoothly varies. However, during a rail to rail condition, the signal show sharp spikes and during the flat condition, the signal 124 is once again essentially zero.

Figure 5:
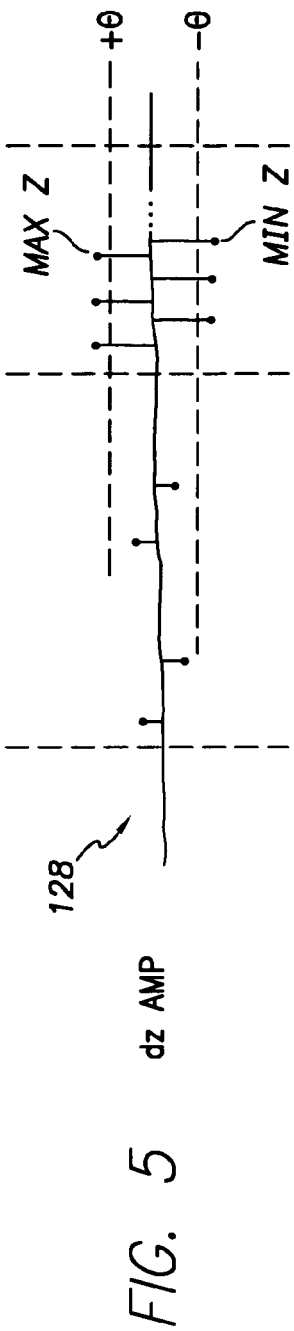
FIG. 5 is a peak amplitude signal of the signal of FIG. 4.

The signal 128 of FIG. 5 shows the maximum and minimum amplitudes of the differential signal 124. As will be noted in FIG. 5, the ALU 64 compares the differential amplitudes to a preset impedance signal differential amplitude threshold $+\theta$ and $-\theta$. The ALU also calculates a maximum impedance signal differential swing amplitude from MAX Z to MIN Z.

Figure 6:
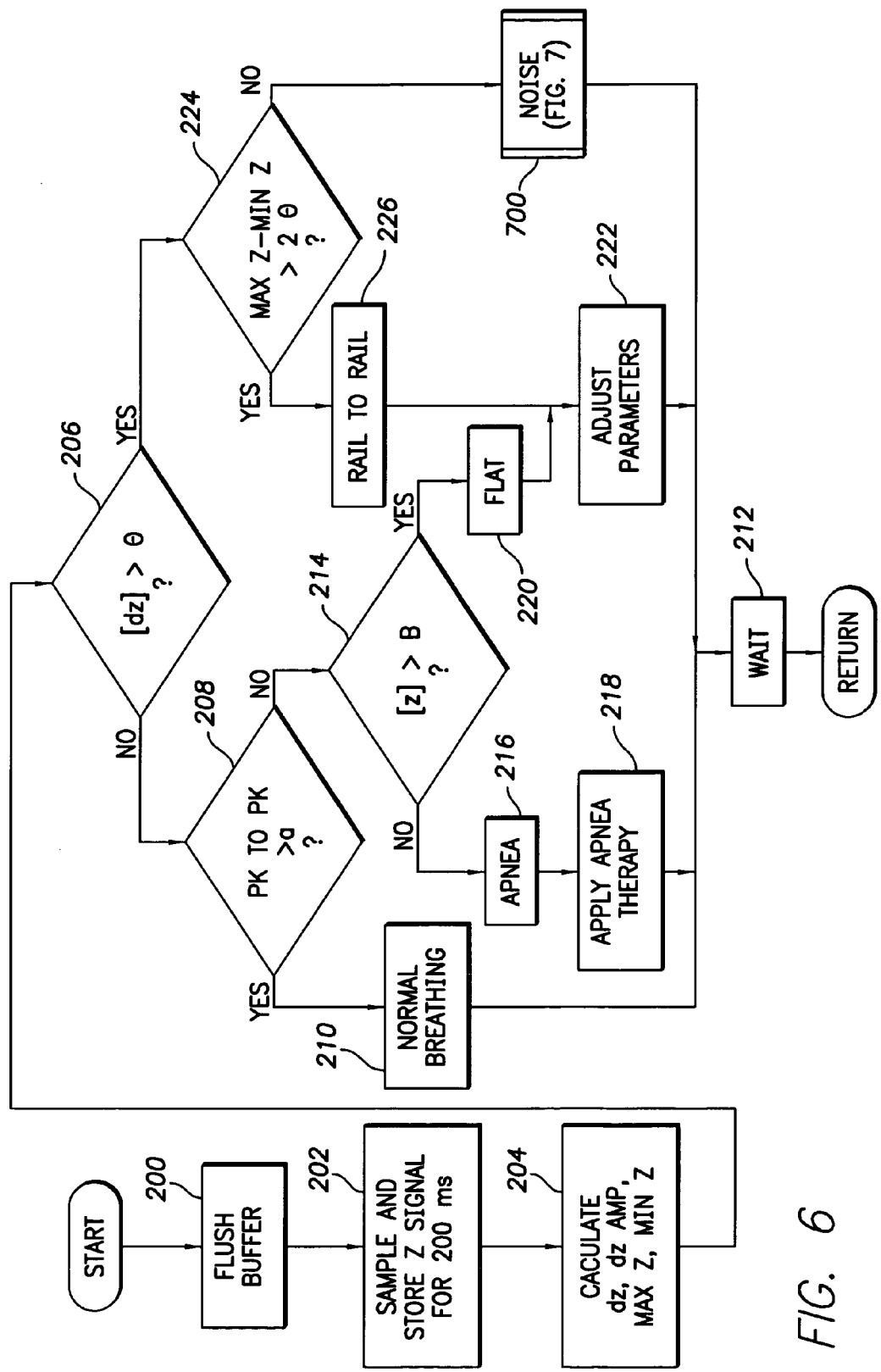
FIG. 6 is a flow diagram describing an overview of one embodiment of the invention.

The foregoing signals may be processed as shown in FIG. 6 to determine if a normal condition exists wherein impedance monitoring operating parameters need not be adjusted or an abnormal condition exists wherein impedance monitoring operating parameters require adjustment. In FIG. 6, the flow chart describes an overview of the operation and novel features implemented in one embodiment of the device 10. In this flow chart, and the flow chart of FIG. 7 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 6 initiates with activity block 200. In activity block 200, a buffer to contain the digital samples of the impedance signal is cleared. After activity block 200, the impedance monitor control 62, in activity block 202, causes the impedance monitor 111 to sample and store the impedance signal (Z) during a sampling interval or window of, for example, 200 milliseconds. To this end, a current pulse of, for example, 2 milliseconds duration is applied to the impedance monitoring electrodes. The input amplifier 113 and impedance measuring circuit 112 generate the impedance signal which is stored in the cleared buffer during the sampling window. Once the impedance signal, such as signal 120 of FIG. 3 is stored, the process advances to activity block 204 wherein the arithmetic logic unit 64 performs the calculations to support the balance of the process. In accordance with activity block 204, the ALU 64 generates the differentiation signal corresponding to the differentiation of the impedance signal. Such a signal is shown, for example, as signal 124 in FIG. 4. Also, the ALU 64 calculates the peak to peak value 121 of the impedance signal, and the maximum and minimum impedance signal differential (MAX Z and MIN Z) as may be seen, for example, in the signal 128 of FIG. 5.

Upon completion of activity block 204, the impedance monitor control 62 advances to decision block 206 wherein the ALU 64 compares the impedance signal differential amplitude absolute value (absolute value of dZ) to a preset impedance differential amplitude threshold ($\theta$). If the impedance signal differential amplitude absolute value is not greater than the preset impedance differential amplitude threshold, the process advances to decision block 208. At this point, the process has already determined that one of a normal breathing, sleep apnea, or saturated or flat condition exists. To differentiate between these conditions, first in decision block 208, the ALU determines if the peak to peak impedance signal amplitude 121 is greater than the minimum impedance amplitude threshold ($\alpha$). If it is, the impedance monitor control 62 in activity block 210 notes a normal breathing condition. The process then advances to activity block 212 wherein a waiting period is implemented before impedance monitoring control is reinitiated.

If in decision block 208 it is determined that the peak to peak impedance signal amplitude is not greater than the minimum impedance amplitude threshold ($\alpha$) the process then advances to decision block 214 wherein it is determined if the impedance signal absolute value is greater than the maximum impedance amplitude threshold ($\beta$). If it isn't, the process advances to activity block 216 to note a sleep apnea condition. Once the sleep apnea condition is noted, the process immediately advances to activity 218 wherein sleep apnea therapy is provided. In accordance with this embodiment, the sleep apnea therapy comprises stimulation of the vagus or phrenic nervous system utilizing electrodes 29 and 30 of lead 25 as previously described. Following application of the therapy in activity block 218, the process then waits in accordance with activity block 212 until reinitiation of the impedance monitoring control.

If in decision block 214 it is determined that the impedance signal absolute value is greater than the maximum impedance amplitude threshold ($\beta$), the process advances to activity block 220 wherein a flat or saturated condition is noted. Once the flat or saturated condition is noted, the process advances to activity block 222 for adjustment of the impedance monitoring parameters. As previously mentioned, the parameters which may be adjusted are the amplitude of the current applied to the impedance monitoring electrodes, the applied current pulse width, the applied current pulse frequency, the gain of input amplifier 113, or the DC offset voltage of the input amplifier 113. Preferably, adjustment of one or more of these parameters will result in the finding of a normal condition not requiring impedance monitor parameter adjustment during the next succeeding impedance monitoring control cycle following the wait period of activity block 212.

If in decision block 206 it is determined that the impedance signal differential absolute value is greater than $\theta$, this indicates that there is either a rail to rail or a noise condition. To distinguish between these conditions, the process advances to decision block 224 wherein the maximum impedance signal differential swing amplitude (MAX Z–MIN Z) is compared to twice the preset impedance signal differential amplitude threshold ($2\theta$). If the outcome of decision block 224 is affirmative, this will indicate a rail to rail condition which is noted in activity block 226. After the rail to rail condition is noted, the process advances to activity block 222 for adjustment of one or more of the impedance monitoring operating parameters previously mentioned. Following activity block 222, the process advances to activity block 212 to implement the wait period before the next impedance monitoring control cycle. Preferably, during the next impedance monitor control cycle, it will be determined that the impedance monitoring condition has returned to a normal condition not in need of parameter adjustment.

If in decision block 224 the outcome is negative, the process then advances to a subroutine 700 to be described hereinafter with reference to FIG. 7 to respond to a noise condition. Once the subroutine is completed, the process advances to the activity block 212 for implementing the wait period prior to the reinitiation of the next impedance monitoring control cycle.

FIG. 7 shows a flow chart describing the subroutine 700 of FIG. 6. The subroutine of FIG. 7 initiates with activity block 702 wherein the noise level detected by the input amplifier 113 is measured during a time when the patient is not breathing. This condition may be determined by the differential of the impedance signal being below a value demonstrative of normal breathing. Once the noise has been measured in activity block 702, the process advances to activity block 704 wherein the gain of the input amplifier 113 is adjusted for a predetermined desired signal to noise ratio. Once the gain is adjusted in activity block 704, the process then advances to activity block 706 wherein the resulting impedance signal is low pass filtered. Following such low pass filtering, the process then advances to decision block 708 wherein it is determined if respiratory modulation exists. In accordance with decision block 708, the impedance monitor control 62 determines if the maximum value of the impedance signal is between a minimum and maximum value, as for example, between $\alpha$ and +$\beta$. If it is not, the process advances to activity 722 for adjustment of one or more of the aforementioned impedance monitoring control operating parameters. If respiratory modulation does exist, the process then advances to decision block 710 to determine if the maximum impedance amplitude is less than a third amplitude (C) which may be a fraction of $\alpha$. If it is, the process advances to activity block 722 for impedance monitoring operating parameter adjustment. If it is not, the process advances to activity block 712 to determine if the maximum impedance amplitude is greater than a fourth amplitude (D) which may be a fraction of $\beta$. If the amplitude is greater than the fourth amplitude (D) the process advances to activity block 722 for parameter adjustment. However, if the outcome of decision block 712 is negative, this indicates that the maximum impedance signal amplitude is within a given range. Hence, the noise subroutine 700 seeks to maintain a maximum impedance signal amplitude within a given range for a given signal to noise ratio.

As will be appreciated by those skilled in the art, the impedance monitor control of the present invention provides a real-time analysis of rail to rail or flat impedance monitoring conditions. It further provides for adjustments in the impedance monitoring operating parameters of current amplitude, current pulse width, input amplifier DC offset, and input amplifier amplifier gain. As a result, the impedance monitor control of the present invention provides a saturation free impedance measurement which avoids saturation signals which may be interpreted as respiratory apnea and the automatic adjustment of impedance measurement parameters.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac device having an impedance monitoring control comprising:
   an impedance monitor comprising a pulse generator that applies a current between a pair of implanted electrodes and an impedance measuring circuit that measures impedance across a pair of implanted electrodes and provides an impedance signal;
   a processor that processes the impedance signal to provide impedance monitoring characteristic results;
   a comparator that compares the impedance monitoring characteristic results to preset standards; and
   a control circuit that varies operating parameters of the impedance monitor responsive to the comparison of the impedance monitoring characteristic results to the present standards;
   wherein the processor includes a differentiator that differentiates the impedance signal and provides an impedance signal differential amplitude absolute value;
   wherein the comparator compares the impedance signal differential amplitude absolute value to a preset impedance signal differential amplitude threshold; and
   wherein the processor provides a maximum impedance signal differential swing amplitude and wherein the comparator, if the impedance signal differential amplitude absolute value is greater than the preset impedance signal differential amplitude threshold, compares the maximum impedance signal differential swing amplitude to a second present impedance signal differential amplitude threshold.

2. The device of claim 1 wherein the control circuit varies the operating parameters if the maximum impedance signal differential swing amplitude is greater than the second present impedance signal differential amplitude.

3. The device of claim 1 wherein the control circuit performs noise processing if the maximum impedance signal differential swing amplitude is less than the second preset impedance signal differential amplitude threshold.

* * * * *